United States Patent
Chen et al.

(10) Patent No.: US 11,160,790 B2
(45) Date of Patent: Nov. 2, 2021

(54) **METHOD OF INHIBITING *CRYPTOCOCCUS* GROWTH USING ELTROMBOPAG**

(71) Applicant: NATIONAL TAIWAN UNIVERSITY, Taipei (TW)

(72) Inventors: Ying-Lien Chen, Taipei (TW); Hao-Tai Ko, Taipei (TW); Li-Hang Hsu, Taipei (TW); Sheng-Yung Yang, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 121 days.

(21) Appl. No.: 16/714,867

(22) Filed: Dec. 16, 2019

(65) Prior Publication Data
US 2021/0121443 A1   Apr. 29, 2021

(30) Foreign Application Priority Data
Oct. 24, 2019  (TW) ................. 10813845.4

(51) Int. Cl.
*A61K 31/4152* (2006.01)
*A61P 31/10* (2006.01)
*A61K 31/436* (2006.01)

(52) U.S. Cl.
CPC ........ *A61K 31/4152* (2013.01); *A61K 31/436* (2013.01); *A61P 31/10* (2018.01)

(58) Field of Classification Search
CPC ... A61K 31/4152; A61K 31/10; A61K 31/436
See application file for complete search history.

(56) References Cited

U.S. PATENT DOCUMENTS

| 2019/0234933 A1* | 8/2019 | Sherris | ................. G01N 33/502 |
| 2020/0254016 A1* | 8/2020 | Oronsky | ............. A61K 31/675 |

OTHER PUBLICATIONS

Ko et al. (Medical Mycology, 2020, 58(4); 493-504 with first publication on Jul. 12, 2019).*
Hao-Tai Ko et al., "Repurposing the thrombopoietin receptor agonist eltrombopag as an anticryptococcal agent", Medical Mycology, myz077, Jul. 12, 2019.

* cited by examiner

*Primary Examiner* — Shirley V Gembeh
(74) *Attorney, Agent, or Firm* — WPAT, PC (57) ABSTRACT

Provided is a method of inhibiting the growth of a fungus using eltrombopag, wherein the fungus is selected from the group consisting of *Cryptococcus*, *Candida glabrata*, and *Trichophyton rubrum*. Also provided are a combination agent that includes eltrombopag and a macrolide calcineurin inhibitor and a method of using the combination agent for inhibiting the growth of *Cryptococcus*. Also provided is a method of inhibiting virulence factor formation in *Cryptococcus* using eltrombopag.

12 Claims, 9 Drawing Sheets

FIG. 1

*C. neoformans* H99

FIG. 2A

*C. deuterogattii* R265

*C. neoformans* H99

FIG. 4C

*C. deuterogattii* R265

Eltrombopag

*C. neoformans* H99

FIG. 6A

Eltrombopag

*C. deuterogattii* R265

METHOD OF INHIBITING *CRYPTOCOCCUS* GROWTH USING ELTROMBOPAG

CROSS-REFERENCE TO RELATED APPLICATION

This application claims priority of Taiwan patent application No. 108138454, filed on Oct. 24, 2019, the content of which is incorporated herein in its entirety by reference.

BACKGROUND OF THE INVENTION

1. Field of the Invention

The present invention relates to a method of inhibiting the growth of fungi using a hydrazine compound. Particularly, the present invention relates to a method of inhibiting the growth of Crypto coccus by using eltrombopag.

2. The Prior Art

Cryptococcosis, mainly caused by *Cryptococcus neoformans/Cryptococcus gattii* species complex, is a globally distributed invasive fungal infection responsible for about 180,000 annual global deaths from cryptococcal meningitis and about 15% of AIDS-related deaths. Human cryptococcosis was recognized as a major health threat with the onset of the AIDS pandemic in the 1980s, during which such fungal infection became a common AIDS-defining illness in patients with greatly reduced T-cell function. In addition, rare cases of cryptococcosis were found in healthy individuals. Cryptococcosis treatment includes monotherapies with 5-flucytosine or fluconazole, and combination therapies with 5-flucytosine plus amphotericin B or high-dose fluconazole.

Unfortunately, amphotericin B is nephrotoxic, and 5-flucytosine is only available in limited areas. Although fluconazole is a comparatively safer and less expensive antifungal drug, the number of fluconazole-resistant isolates is increasing in South Africa and some other countries. Despite the urgent need for safe and effective anti-cryptococcal agents, no new antifungal agents for cryptococcosis have been approved for more than 25 years due to the time-consuming process of drug development.

Drug repurposing is an alternative to the process of drug discovery. Some of the examples of using existing drugs as antifungal agents are the immunosuppressive calcineurin inhibitors, such as FK506 and cyclosporine, which are compounds in the macrolide and cyclopeptide classes, respectively. The two compounds, as monotherapy or in combination therapy, show anti-cryptococcal activity. However, these drugs have toxic side effects, including nephrotoxicity and neurotoxicity. Therefore, it is of necessity to develop safer and more effective drugs to treat cryptococcal infections.

Eltrombopag is a low-molecular-weight and synthetic non-peptide molecule that serves as an agonist of the thrombopoietin receptor. It improves platelet production by stimulating megakaryocytes in the bone marrow to multiply and differentiate. It has been shown to effectively increase platelet counts and reduce bleeding symptoms in patients with chronic immune thrombocytopenic purpura (ITP). Thus, eltrombopag was initially approved by the US Food and Drug Administration (FDA) in 2008 for treating patients with ITP. However, there is no investigation on the antifungal activity of eltrombopag.

SUMMARY OF THE INVENTION

In one aspect, the present invention provides a method of inhibiting growth of a fungus, including contacting the fungus with an effective amount of eltrombopag (as shown in formula (I) below; herein also referred to as ETP), wherein the fungus is selected from the group consisting of *Cryptococcus*, *Candida glabrata*, and *Trichophyton rubrum*.

formula (I)

In one embodiment of the invention, the *Cryptococcus* is *Cryptococcus neoformans*, *Cryptococcus gattii*, or *Cryptococcus deuterogattii*.

In another aspect, the present invention provides a combination agent for inhibiting growth of *Cryptococcus*, including eltrombopag and a macrolide calcineurin inhibitor. Also provided is a method of inhibiting growth of *Cryptococcus*, including contacting the *Cryptococcus* with the combination agent. The macrolide calcineurin inhibitor is a calcineurin inhibitor containing a macrolide lactone structure.

In one embodiment of the invention, the macrolide calcineurin inhibitor is tacrolimus (also called FK506) or an analog thereof. The analog refers to a compound with a structure similar to that of FK506.

In still another aspect, the present invention provides a method of inhibiting virulence factor formation in *Cryptococcus*, comprising contacting the *Cryptococcus* with an effective amount of eltrombopag.

In one embodiment of the invention, the virulence factor formation is biofilm formation, capsule formation, or melanin production.

The invention discloses that eltrombopag can be used as a relatively broad-spectrum antifungal agent capable of inhibiting the growth of various *Cryptococcus* species and other fungi such as *Candida glabrata* and *Trichophyton rubrum*. Particularly, eltrombopag is able to inhibit the growth of clinical and azole-resistant *Cryptococcus* strains, and thus can be utilized to develop antifungal therapies in place of azoles. In addition, the combination of eltrombopag and a macrolide calcineurin inhibitor demonstrates synergism in inhibiting the growth of *Cryptococcus*, whereby decreasing the required amounts of the two drugs to inhibit fungi. Eltrombopag can also inhibit the formation of various virulence factors in *Cryptococcus*. Therefore, the invention provides a new strategy for treatment of fungal infections, particularly cryptococcal infections.

The present invention is further explained in the following examples. It is understood that the examples given below do not limit the scope of the invention, and it will be evident to those skilled in the art that modifications can be made without departing from the scope of the appended claims.

BRIEF DESCRIPTION OF THE DRAWINGS

The present invention will be apparent to those skilled in the art from the following detailed description of the preferred embodiments, with reference to the accompanying drawings, in which.

DETAILED DESCRIPTION OF THE PREFERRED EMBODIMENT

The invention provides applications of eltrombopag in methods or agents against *Cryptococcus*, including: (1) a method of inhibiting the growth of a fungus using eltrombopag, wherein the fungus is selected from the group consisting of *Cryptococcus*, *Candida glabrata*, and *Trichophyton rubrum*; (2) a combination agent that includes eltrombopag and a macrolide calcineurin inhibitor and a method of using the combination agent for inhibiting growth of *Cryptococcus*; and (3) a method of inhibiting virulence factor formation in *Cryptococcus* using eltrombopag. The following examples demonstrate the inhibitory effect of eltrombopag on the growth of several pathogenic fungi, the synergistic effect of eltrombopag in combination with the macrolide calcineurin inhibitor FK506 on inhibition of *Cryptococcus* growth, and the ability of eltrombopag to interfere with virulence factor formation in *Cryptococcus* such as biofilm formation, capsule formation, and melanin production.

Definition

Numerical quantities provided herein are approximated, experimental values that may vary within 20 percent, preferably within 10 percent, and most preferably within 5 percent. Thus, the terms "about" and "approximately" refer to within 20 percent, preferably within 10 percent, and most preferably within 5 percent of a given value or range.

Unless otherwise defined, the term "fungus" or "fungi" as used herein includes yeasts and filamentous fungi. The yeasts include *Cryptococcus* spp. and *Candida* spp. The filamentous fungi include *Aspergillus* spp., *Fusarium* spp., and *Trichophyton* spp.

Unless otherwise defined, the term "*Cryptococcus*" as used herein refers to the fungi of the *Cryptococcus* genus, including but not limited to *Cryptococcus neoformans*, *Cryptococcus gattii*, *Cryptococcus deuterogattii*, *Cryptococcus albidus*, *Cryptococcus laurentii*, *Cryptococcus curvatus*, and *Cryptococcus humicola*.

As used herein, the term "virulence factor(s)" refers to factor(s) that *Cryptococcus* possess to increase their pathogenicity. The virulence factors include biofilms, capsules, metabolites, melanin or mannitol, and other substances that help *Cryptococcus* survive and proliferate in the host, such as proteases and phospholipases. Thus, the expression "virulence factor formation in *Cryptococcus*" refers to the forming process of these virulence factors, such as biofilm formation, capsule formation, and melanin production.

Unless otherwise defined, the term "agent(s)" as used herein includes medicaments or pharmaceutical compositions that are administered to animals including human beings, and also includes chemical products for use in objects other than animals, for example, antimicrobials for non-living objects (such as medical devices), water, soil, or other environmental areas.

As used herein, the term "combination agent" refers to a combination of two or more drugs, and the combination generates a synergistic effect. One example of the combination agent is the combination of eltrombopag and FK506. The inhibitory effect of such combination on the growth of *Cryptococcus* is greater than the fungistatic effect of either one of the constituent drugs alone.

The medicament or pharmaceutical composition described herein may be formulated, by techniques well known to those skilled in the art, into a dosage form suitable for parenteral or oral administration. The dosage form includes, but not limited to, injections (for example, sterile aqueous solution or dispersion), powders, tablets, troches, lozenges, pills, capsules, dispersible powders, granules, solutions, suspensions, emulsions, syrups, elixirs, slurries, and the like.

The pharmaceutical composition described herein may be administered via parenteral routes, including but not limited to intraperitoneal injection, subcutaneous injection, intramuscular injection, and intravenous injection.

The pharmaceutical composition described herein may contain a pharmaceutically acceptable carrier that is widely used in the field of pharmaceutical manufacturing. The pharmaceutically acceptable carrier includes one or more agents selected from the group consisting of solvents, emulsifiers, suspending agents, decomposers, binding agents, excipients, stabilizing agents, chelating agents, diluents, gelling agents, preservatives, lubricants, absorption delaying agents, liposomes, and the like. The selection and amount for use of these agents are based on conventional techniques within the profession of those skilled in the art.

The aforementioned pharmaceutically acceptable carrier may include a solvent selected from the group consisting of water, normal saline, phosphate buffered saline (PBS), a sugar-containing solution, an aqueous solution containing alcohol, and combinations thereof.

As used herein, the expression "an effective amount" refers to the amount of drug required to inhibit fungal growth or to inhibit virulence factor formation in *Cryptococcus*. As appreciated by those skilled in the art, the effective amount will vary depending on the route of administration, the use of excipients, and co-administration with other therapies.

As used herein, the term "subject" as used herein refers to mammals in need of treatment for a fungal infection such as cryptococcosis or cryptococcal meningitis. The subject can be human or non-human, such as a primate, mouse, dog, cat, cow, horse, rabbit, pig, and the like.

Materials and Methods
Materials

Yeast extract, glucose, peptone, and agar were purchased from Bioshop (Burlington, Ontario, Canada). Dextrose was purchased from Bioman (New Taipei City, Taiwan). Potato infusion was purchased from HiMedia (Mumbai, India). RPMI 1640 medium, 3-morpholinopropane-1-sulfonic acid (MOPS), dimethyl sulfoxide (DMSO), and XTT-based In Vitro Toxicology Assay Kit (TOX2; XTT means 2,3-bis-[2-methoxy-4-nitro-5-sulfophenyl]-2H-tetrazolium-5-carboxanilide inner salt) were purchased from Sigma-Aldrich (St. Louis, Mo., USA). Eltrombopag, amphotericin B, fluconazole, and FK506 were purchased from Selleckchem (Houston, Tex., USA). Magnesium sulfate was purchased from Santoku Chemical (Tokyo, Japan). Potassium dihydrogen phosphate was purchased from Shimakyu's Pure Chemicals (Osaka, Japan). Glycine was purchased from Omics Bio. (New Taipei City, Taiwan). Thiamine hydrochloride was purchased from W. S. Simpson (Easton, Mass., USA).

Strains and Growth Media

Fungal strains described in the following examples can be purchased from the American Type Culture Collection (ATCC; Manassas, Va., USA) or obtained from the laboratories that disclosed the strain in academic journals. For example, *Cryptococcus neoformans* H99 was disclosed by Perfect J R et al (see Perfect J R et al. *J Clin Microbiol*. 1993; 31:3305-3309); *Cryptococcus neoformans* T1 and *Cryptococcus neoformans* 89-610 were disclosed by Odom A et al (see Odom A et al. *Antimicrob Agents Chemother*. 1997; 41: 156-161); *Cryptococcus deuterogattii* 8265 and *Cryptococcus deuterogattii* R272 were disclosed by Kidd S E et al (see Kidd S E et al. *Proc Natl Acad Sci USA*. 2004; 101: 17258-17263) or Hagen F et al (see Hagen F et al. *Fungal Genet Biol*. 2015; 78: 16-48); *Cryptococcus gattii* WM276 was disclosed by Kidd S E et al (see Kidd S E et al. *Eukaryot Cell*. 2005; 4: 1629-1638); *Candida albicans* SC5314 was disclosed by Jones T et al (see Jones T et al. *Proc Natl Acad Sci USA*. 2004; 101: 7329-7334); *Candida tropicalis* MYA3404, *Candida parapsilosis* ATCC22019, and *Candida lusitaniae* ATCC42720 were disclosed by Butler G et al (see Butler G et al. *Nature*. 2009; 459: 657-662); *Candida krusei* ATCC6258 was disclosed by Forastiero A (see Forastiero A et al. *Antimicrobial agents and chemotherapy*. 2015; 59: 6975-6982); *Candida glabrata* CBS138 was disclosed by Dujon B et al (see Dujon B et al. Genome evolution in yeasts. *Nature*. 2004; 430: 35-44); *Aspergillus fumigatus* AF293 was disclosed by Nierman W C et al (see Nierman W C et al. *Nature*. 2005; 438: 1151-1156); *Fusarium solani* Fungus 111-6 was disclosed by Hsu L H et al (see Hsu L H et al. *Int J Antimicrob Agents*. 2017; 49: 740-748); and *Trichophyton rubrum* MYA4438 was disclosed by Jo Siu W J et al (see Jo Siu W J et al. *Antimicrob Agents Chemother*. 2013; 57: 1610-1616).

*Cryptococcus* and *Candida* species were cultured in yeast extract-peptone-dextrose (YPD) medium (containing 1% yeast extract, 2% peptone, 2% glucose, and optionally 2% agar for preparation of an agar plate). *Aspergillus, Fusarium*, and *Trichophyton* species were cultured on potato dextrose agar (PDA) plate (containing 2% potato infusion, 0.2% dextrose, and 1.5% agar). A microdilution assay was performed to determine minimum inhibitory concentration (MIC), minimum fungicidal concentration (MFC), and fractional inhibitory concentration (FIC) index (FICI) using RPMI 1640 medium buffered with MOPS. Minimal medium (containing 15 mM glucose, 10 mM magnesium sulfate, 29.4 mM potassium dihydrogen phosphate, 13 mM glycine, and 3 μM thiamine hydrochloride; pH 5.5) was used for capsule size assay and melanization assay.

Example 1

Antifungal Activity of Eltrombopag

To investigate the inhibitory effects of eltrombopag on the growth of fungi, microdilution assays (based on the CLSI standards M27-A3 and M38-A2) were performed with multiple pathogenic yeasts and filamentous fungi including *Cryptococcus, Candida, Aspergillus, Fusarium*, and *Trichophyton* (TABLE 1). Briefly, yeast or filamentous fungi strains at a final concentration of about $10^3$ cfu/mL were inoculated in RPMI 1640 medium containing two-fold serially diluted eltrombopag (started at 64 mg/L). In addition, fungal cultures without eltrombopag were used as positive controls, while media without fungal cells and eltrombopag were used as negative controls. The 96-well plates loaded with the aforementioned cultures were incubated at 35° C. for 48 hours, and the growth of cells in each well was examined to determine the minimum inhibitory concentration (MIC) of eltrombopag, which was the lowest drug concentration at which there was no visible cell growth. Thereafter, 3 μL of the fungal culture from each well of the 96-well plates was spotted onto eltrombopag-free YPD (for yeasts) or PDA (for filamentous fungi) agar plates, which were then incubated at 35° C. for 48 hours to examine colony formation Minimum fungicidal concentration (MFC) was determined to be the lowest drug concentration at which no colonies formed. The assays were performed in triplicate.

According to TABLE 1, the MIC of eltrombopag against multiple *C. neoformans/C. gattii* was approximately 0.125 mg/L at 35° C. Of note, two *C. neoformans* strains (T1 and 89-610) known to be clinically resistant to azoles were also susceptible to eltrombopag with MICs of 0.125 mg/L, indicating that eltrombopag uses a mode of action distinct from that of azoles to combat *Cryptococcus*.

TABLE 1

| Strain | Isolate | MIC (mg/L) | MFC (mg/L) |
| --- | --- | --- | --- |
| *Cryptococcus neoformans* H99 | Clinical | 0.125 | >64 |
| *Cryptococcus neoformans* T1 | Clinical | 0.125 | >64 |
| *Cryptococcus neoformans* 89-610 | Clinical | 0.125 | >64 |
| *Cryptococcus deuterogattii* R265 | Clinical | 0.125 | >64 |

TABLE 1-continued

| Strain | Isolate | MIC (mg/L) | MFC (mg/L) |
|---|---|---|---|
| *Cryptococcus deuterogattii* R272 | Clinical | 0.125 | >64 |
| *Cryptococcus gattii* WM276 | Environmental | 0.125 | >64 |
| *Candida albicans* SC5314 | Clinical | >64 | >64 |
| *Candida tropicalis* MYA3404 | Clinical | 64 | >64 |
| *Candida krusei* ATCC6258 | Clinical | 64 | >64 |
| *Candida parapsilosis* ATCC22019 | Clinical | 64 | >64 |
| *Candida lusitaniae* ATCC42720 | Clinical | 64 | >64 |
| *Candida glabrata* CBS138 | Clinical | 0.25 | >64 |
| *Aspergillus fumigatus* AF293 | Clinical | >64 | >64 |
| *Fusarium solani* Fungus III-6 | Clinical | >64 | >64 |
| *Trichophyton rubrum* MYA4438 | Clinical | 0.5 | >64 |

According to TABLE 1, although eltrombopag did not show high antifungal activity against most *Candida* species (MIC≥64 mg/1), it did inhibit *Candida glabrata* with an MIC of about 0.25 mg/L. Moreover, eltrombopag exhibited antifungal activity against *Trichophyton rubrum* (MIC of about 0.5 mg/L), a dermatophytic fungus that commonly causes skin infections in animals and humans. However, eltrombopag had no antifungal activity against *Aspergillus fumigatus* or *Fusarium solani*. Furthermore, the MFCs of higher than 64 mg/L for the *Cryptococcus* species, *C. glabrata*, and *T. rubrum* indicated that eltrombopag inhibited the growth of these fungi by actions except fungicidal effects.

Example 2

Inhibitory Effects of Eltrombopag on the Growth of *Cryptococcus*

To study the inhibitory effects of eltrombopag on the growth of *Cryptococcus*, *C. neoformans* H99 cells were cultured overnight at 30° C. and then washed twice with double-distilled water. The cells were diluted to 0.0005 $OD_{600}$/mL with RPMI 1640 medium, and 5 mL of the cell suspension was treated with eltrombopag at 0.5, 0.25, 0.125, 0.06, or 0 mg/L and incubated at 37° C. with shaking at 150 rpm for 4 days. The cell density of the suspensions was measured every 12 hours with a SpectraMax190 microplate reader (Molecular Devices), and growth curves were plotted using Prism 5.03 (GraphPad Software, San Diego, Calif., USA). The experiments were performed in triplicate, and the results were presented as mean±standard deviation.

Figure 1:
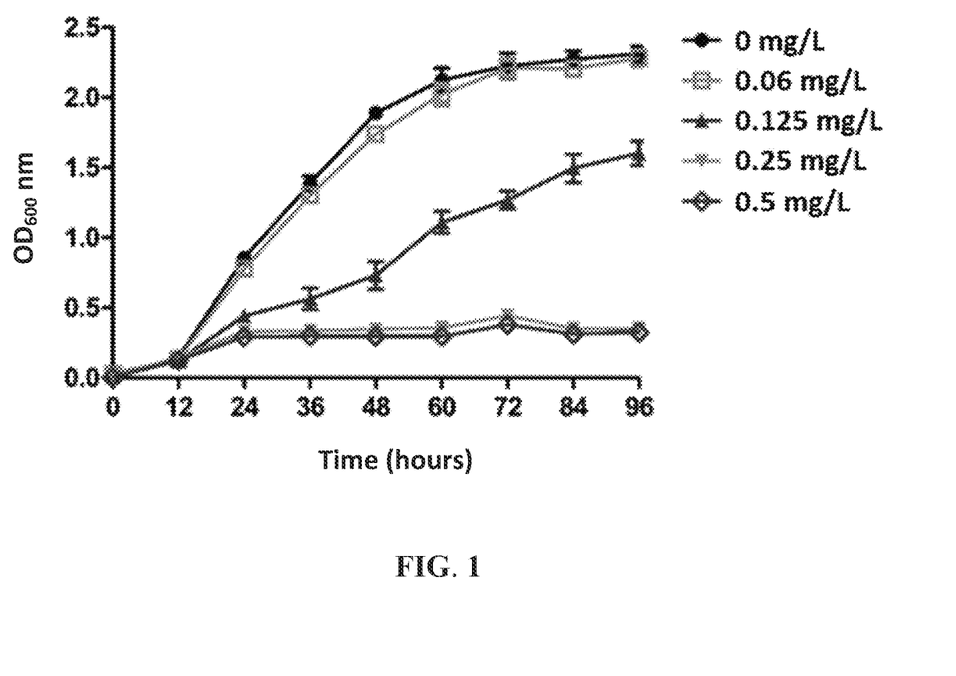
FIG. 1 shows the growth kinetics of *Cryptococcus neoformans* H99 treated with eltrombopag at various concentrations.

FIG. 1 shows the growth kinetics of *C. neoformans* H99 with eltrombopag at various concentrations. According to the figure, eltrombopag inhibited the growth of *C. neoformans* in a dose-dependent manner. In the presence of 0.25 mg/L or 0.5 mg/L eltrombopag, the static growth of *C. neoformans* was maintained after incubation at 37° C. for 96 hours, indicating that eltrombopag exhibited fungistatic activity.

A disk diffusion susceptibility assay was performed to further investigate the fungistatic activity of eltrombopag at different temperatures. Briefly, *C. neoformans* H99 or *C. deuterogattii* 8265 was cultured overnight at 30° C., and 100 μL of the culture (at an $OD_{600}$ of about 0.1) was spread on RPMI 1640 agar plates. Paper disks (with a diameter of 6 mm) were then placed on these agar plates, and either 10 μg eltrombopag (dissolved in 5 μL DMSO) or 5 μL DMSO (control) was added to each disk. The agar plates were incubated at 25° C., 30° C., or 37° C. for 48 hours and photographed.

Figure 2A:
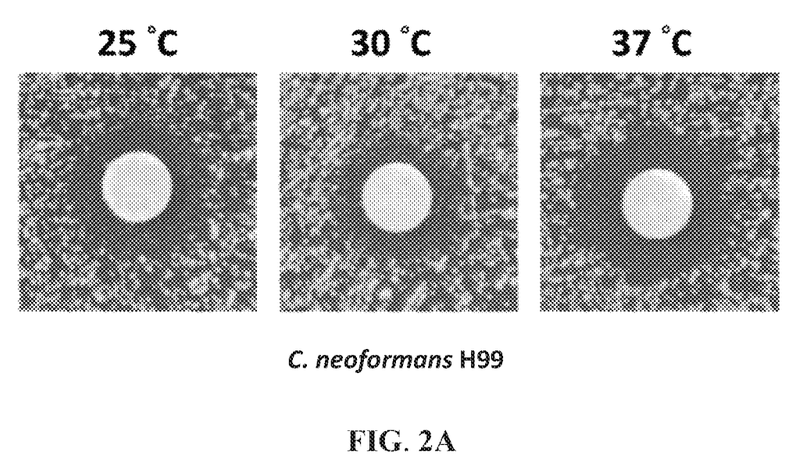
FIG. 2A shows the images of *C. neoformans* H99 growing on agar plates in a disk diffusion susceptibility assay, wherein the disk was loaded with 10 μg eltrombopag.
Figure 2B:
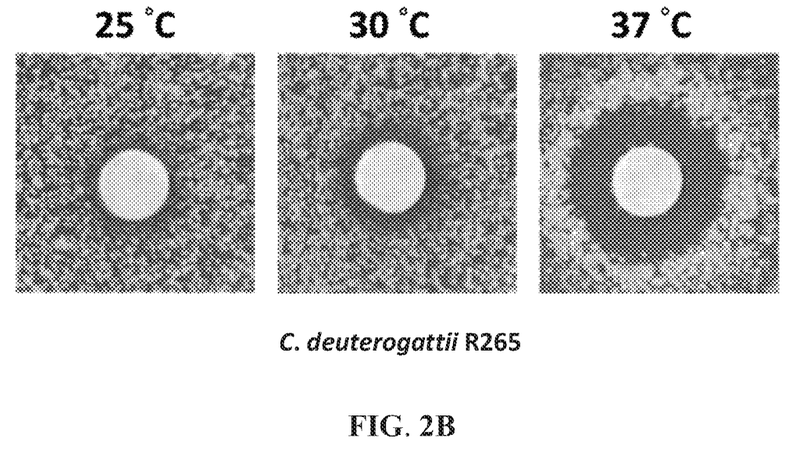
FIG. 2B shows the images of *Cryptococcus deuterogattii* 8265 growing on agar plates in a disk diffusion susceptibility assay, wherein the disk was loaded with 10 μg eltrombopag.

FIG. 2A and FIG. 2B are the images of agar plates where *C. neoformans* H99 and *C. deuterogattii* 8265 were grown, respectively, in the assay. The images show that the *Cryptococcus* colonies on the plates disappeared around the eltrombopag-loaded disks. Interestingly, when compared with the inhibition zones formed at 30° C. or 25° C., significantly larger inhibition zones were observed at 37° C., demonstrating that eltrombopag has greater anti-cryptococcal activity at human body temperatures.

Example 3

Effects of Eltrombopag on the Cellular Ultrastructure of *Cryptococcus*

To study the effects of eltrombopag on the cellular structure of *Cryptococcus*, *C. neoformans* H99 or *C. deuterogattii* 8265 was cultured in RPMI 1640 medium containing 0.06 or 0 mg/L eltrombopag at 37° C. for 48 hours, and the cell morphology was examined by scanning electron microscopy (FEI Inspect S SEM, USA).

Figure 3A:
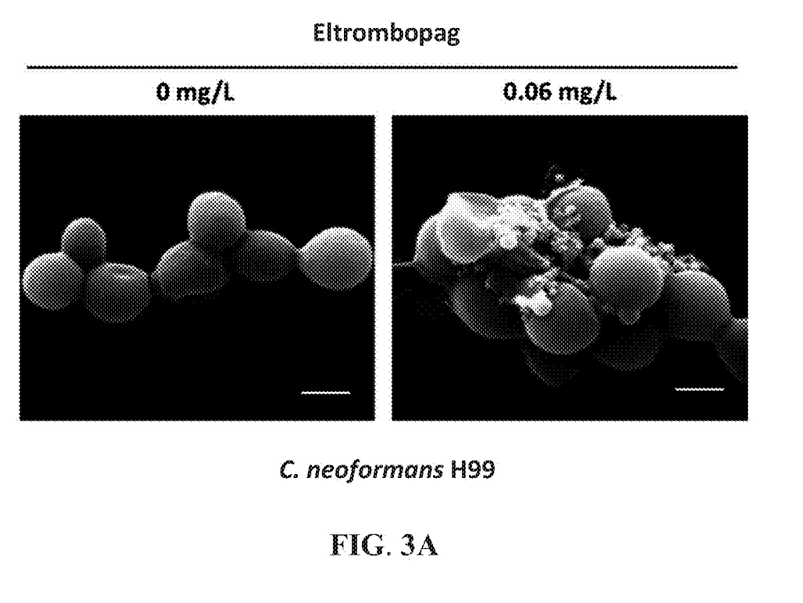
FIG. 3A shows the SEM images of *C. neoformans* H99 cells after incubation for 48 hours in the presence or absence of eltrombopag; the scale bars represent 2 μm.
Figure 3B:
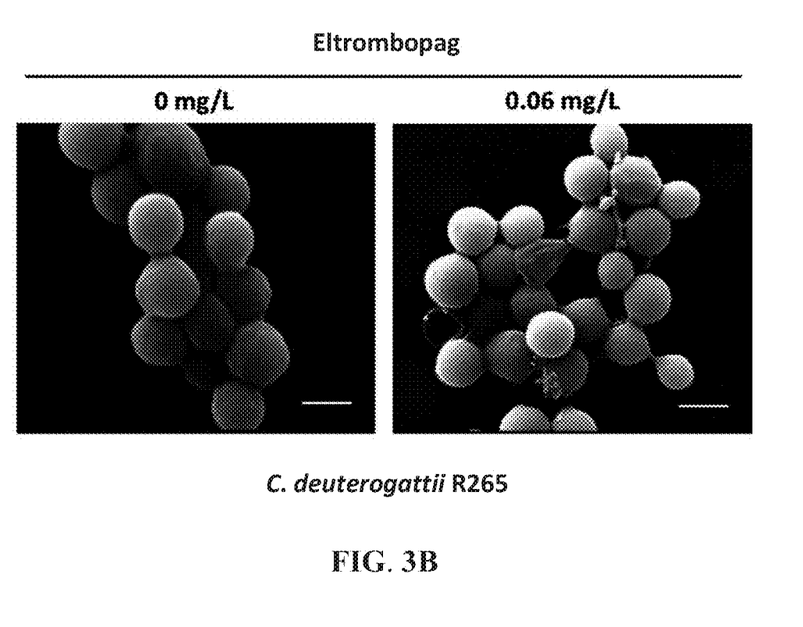
FIG. 3B shows the SEM images of *C. deuterogattii* R265 cells after incubation for 48 hours in the presence or absence of eltrombopag; the scale bars represent 2 μm.

FIG. 3A and FIG. 3B are the images of *C. neoformans* H99 and *C. deuterogattii* R265 cells after incubation for 48 hours in the presence or absence of eltrombopag. According to FIGS. 3A-3B, both of the eltrombopag-treated *Cryptococcus* species produced a small number of incomplete buds on the cell surface. This phenomenon was not observed in cryptococcal cells without eltrombopag treatment. The results indicate that eltrombopag can inhibit the growth of *Cryptococcus* by affecting the development of normal cellular structures (such as the cell membrane or cell wall).

Example 4

Eltrombopag Displays Synergy with FK506 Against *Cryptococcus*

Amphotericin B plus 5-flucytosine or fluconazole are combinations often used to treat cryptococcal meningitis. To investigate the synergy between eltrombopag and existing antifungal drugs or other drugs, a checkerboard titration assay was performed on *Cryptococcus*. Briefly, *C. neoformans* H99 and *C. deuterogattii* R265 cells were cultured overnight at 30° C. and then washed twice with double-distilled water. The cells were diluted to $10^3$ cfu/mL with RPMI 1640 medium, and 100 μL of the cell suspension was added to each well of a 96-well polystyrene plate. The cells in each well were administered with eltrombopag, two-fold serially diluted from 8 to 0.015 mg/L, and an indicated drug (i.e., fluconazole, amphotericin B, FK506, or cyclosporine A), two-fold serially diluted from 16 to 0.25 mg/L. After incubation at 30° C. for 48 hours, the growth of cells under different treatments was assessed by measuring the light absorbance at 600 nm ($OD_{600}$). This assay allows the determination of fractional inhibitory concentration index (FICI): ($MIC_{combined}$ of drug A/$MIC_{alone}$ of drug A)+ ($MIC_{combined}$ of drug B/$MIC_{alone}$ of drug B). After the checkerboard titration assay, the cells (3 μL) in the 96-well plate were transferred to drug-free YPD agar plates. After incubation at 30° C. for 48 hours, the agar plates were photographed and assessed for cell viability.

Figure 4A:
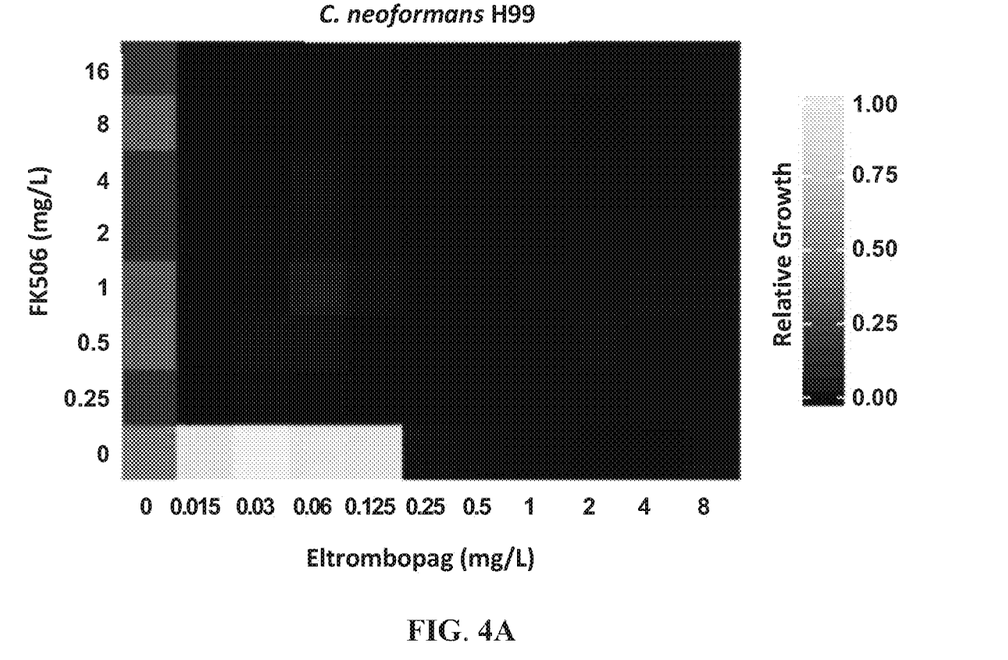
FIG. 4A shows the growth performance of *C. neoformans* H99 after a checkerboard titration assay was performed with eltrombopag and FK506.
Figure 4B:
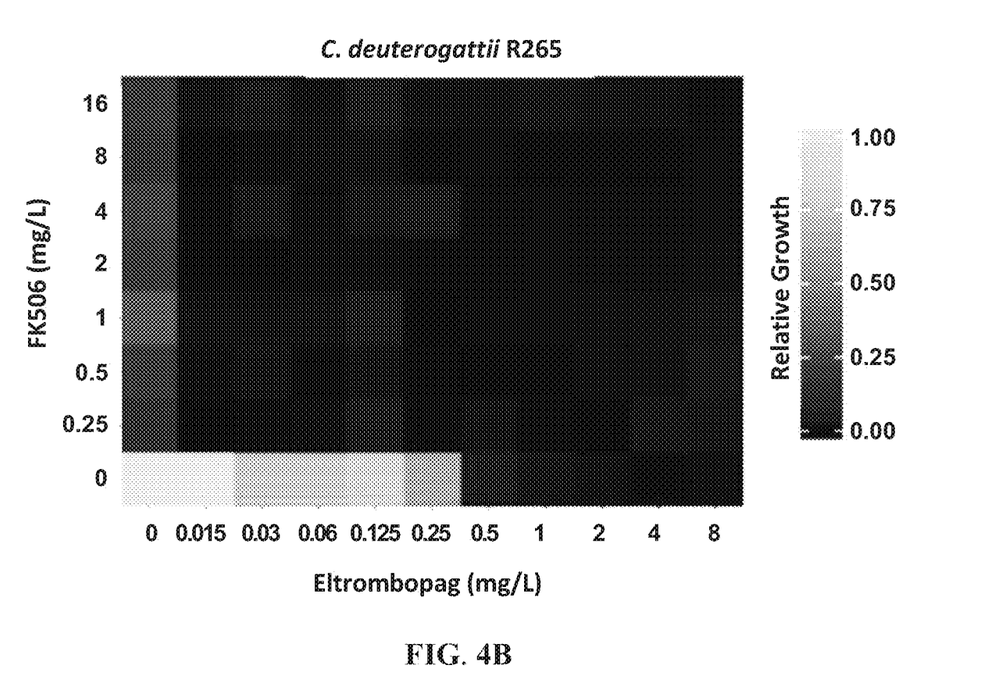
FIG. 4B shows the growth performance of *C. deuterogattii* 8265 after a checkerboard titration assay was performed with eltrombopag and FK506.

FIG. 4A and FIG. 4B respectively show the growth performance of *C. neoformans* H99 and *C. deuterogattii* 8265 after the checkerboard titration assay was performed with eltrombopag and FK506; light gray indicates fungal growth, and black indicates lack of fungal growth. TABLE 2 shows the FICIs values for the various drug combinations; an FICI≤0.5 indicates synergy, an FICI >4.0 indicates antagonism, and an FICI >0.5-4 indicates no interaction. According to TABLE 2, no synergy was found between eltrombopag (ETP) and existing antifungal drugs such as amphotericin B (AMB), fluconazole (FLC), or (cyclosporine A), whereas eltrombopag exerted synergistic antifungal activity with FK506, as shown in FIGS. 4A-4B. TABLE 2 shows that when the ETP+FK506 combination was applied, an FICI of 0.07 for *C. neoformans* H99 and an FICI of 0.03 for *C. deuterogattii* R265 were observed. The results indicate that the combination of eltrombopag and FK506 allows each of the constituents to display antifungal activity at a significantly lower concentration. Accordingly, the combination of eltrombopag and a macrolide calcineurin inhibitor can be used as a combination agent for inhibiting growth of *Cryptococcus*. The rationale for the choice of calcineurin inhibitors to test the combination effect with eltrombopag was based on the observation by the inventors that the antifungal effect of eltrombopag was associated with the calcineurin pathway (data not shown).

Figure 4C:
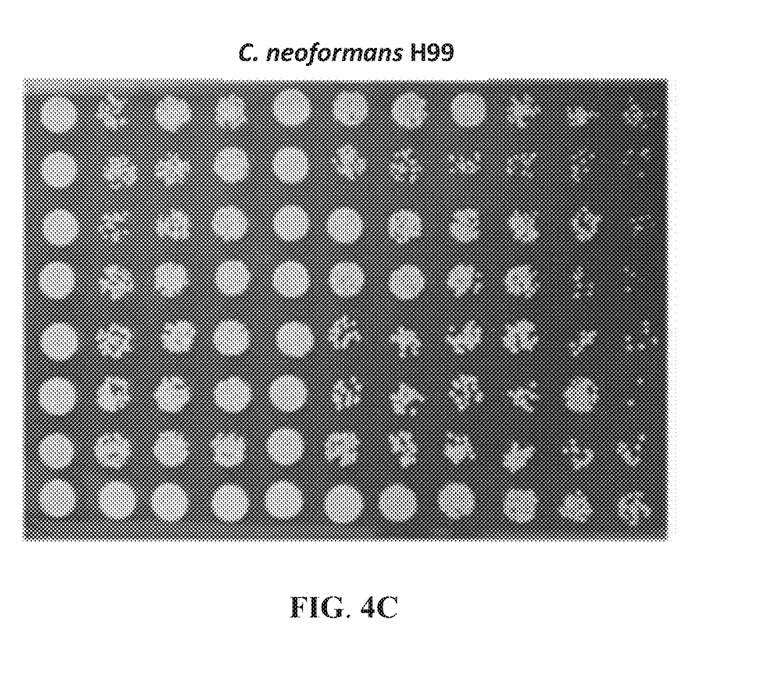
FIG. 4C shows the images of the *C. neoformans* H99 cells obtained from the checkerboard titration assay shown in FIG. 4A and further incubated without drug for 48 hours.
Figure 4D:
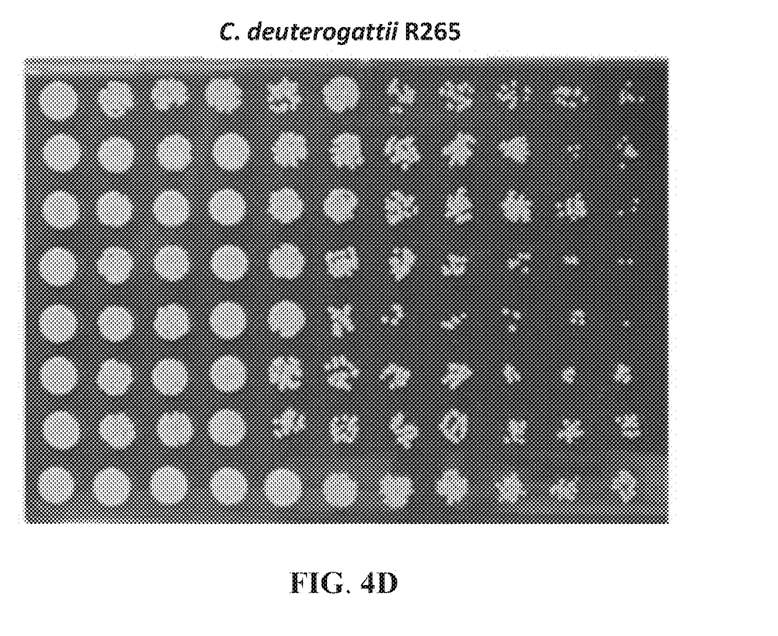
FIG. 4D shows the images of the *C. deuterogattii* R265 cells obtained from the checkerboard titration assay shown in FIG. 4B and further incubated without drug for 48 hours.

FIG. 4C and FIG. 4D are the images of the *Cryptococcus* cells obtained from the checkerboard titration assay shown in FIG. 4A and FIG. 4B, respectively, and further incubated without drug for 48 hours. According to FIGS. 4C-4D, the two *Cryptococcus* species were still able to grow after incubation at 30° C. for 48 hours, suggesting that the synergy between eltrombopag and FK506 did not convert the fungistatic activity into fungicidal activity.

measuring the light absorbance at 492 nm. The experiments were performed in triplicate, and the results were presented as mean±standard deviation. Statistical significance for the data sets was determined using a two-tailed t test.

Figure 5A:
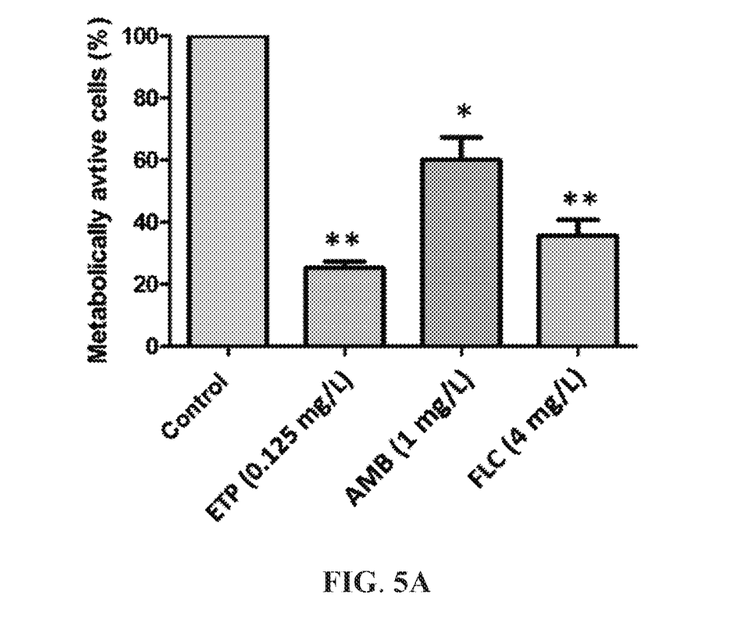
FIG. 5A shows the metabolic activity of *C. neoformans* H99 treated with eltrombopag (ETP), amphotericin B (AMB), or fluconazole (FLC) at their respective minimum inhibitory concentration for 24 hours.

FIG. 5A shows the metabolic activity of *C. neoformans* H99 treated with eltrombopag (ETP), amphotericin B (AMB), or fluconazole (FLC) at their respective minimum inhibitory concentration (MICs) for 24 hours; the values are expressed as percentages compared to the metabolic activity of the control group; * and ** indicate P<0.05 and P<0.01, respectively, compared with the control group. According to FIG. 5A, the metabolic activity of *C. neoformans* was reduced by more than 70% with 0.125 mg/L eltrombopag treatment compared to the control group. It was also found that amphotericin B and fluconazole at their respective MICs were less effective than eltrombopag in reducing the metabolic activity of *C. neoformans* biofilms.

Figure 5B:
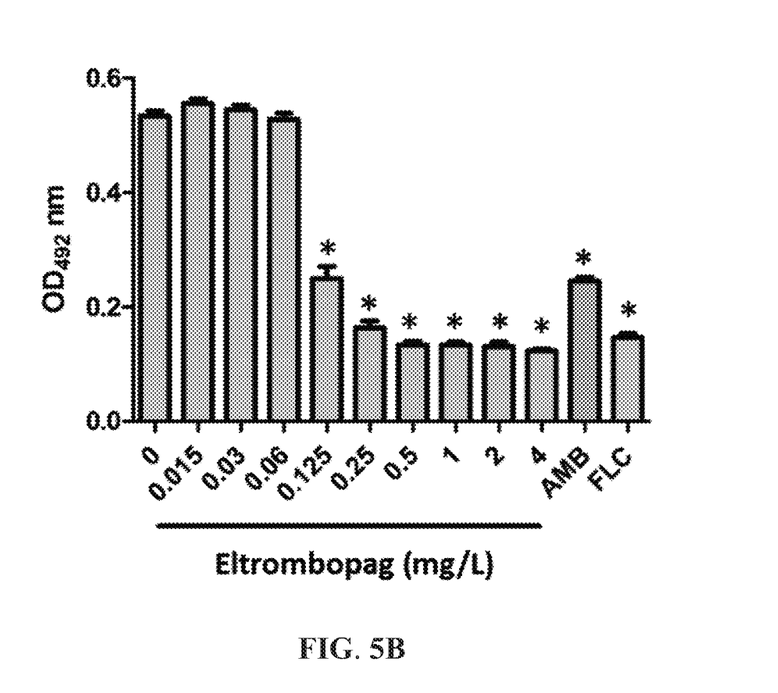
FIG. 5B shows the metabolic activity of *C. neoformans* H99 treated with two-fold serially diluted eltrombopag, amphotericin B (AMB), or fluconazole (FLC) for 48 hours.

FIG. 5B shows the metabolic activity of *C. neoformans* H99 treated with two-fold serially diluted eltrombopag (from 4 to 0.015 mg/L), amphotericin B (1 mg/L), or fluconazole (4 mg/L) for 48 hours; the level of metabolic activity is expressed as $OD_{492}$; * indicates P<0.05 compared with the control group (0 mg/L eltrombopag). According to

TABLE 2

| Strain | MIC$_{alone}$ (mg/L) | | | | |
|---|---|---|---|---|---|
| | ETP | FLC | AMB | FK506 | CsA |
| *C. neoformans* H99 | 0.25 | 4 | 1 | >16 | >16 |
| *C. deuterogattii* R265 | 0.5 | 16 | 1 | >16 | >16 |

| Strain | MIC$_{combined}$ (mg/L) | | | |
|---|---|---|---|---|
| | ETP, FLC | ETP, AMB | ETP, FK506 | ETP, CsA |
| *C. neoformans* H99 | 0.03, 8 | 0.03, 0.5 | 0.015, 0.25 | 0.25, 2 |
| *C. deuterogattii* R265 | 0.03, 16 | 0.03, 1 | 0.015, 0.25 | 1, 16 |

| Strain | FICI | | | |
|---|---|---|---|---|
| | ETP + FLC | ETP + AMB | ETP + FK506 | ETP + CsA |
| *C. neoformans* H99 | 2.06 | 0.56 | 0.07 | 0.56 |
| *C. deuterogattii* R265 | 1.06 | 1.06 | 0.03 | 2.5 |

Example 5

Eltrombopag Impairs Biofilm Formation in *C. neoformans*

*Cryptococcus* biofilms, which are composed of *Cryptococcus* cells and extracellular matrix, enhance the tolerance of *Cryptococcus* to antifungal agents (such as amphotericin B) and host defense mechanisms. To assess whether eltrombopag impacts biofilm formation in *Cryptococcus*, an XTT-reduction assay was used to measure the metabolic activity of *C. neoformans* cells treated with eltrombopag at 37° C. Briefly, *C. neoformans* H99 cells were cultured in YPD medium at 30° C. overnight. The cells were washed twice with phosphate buffered saline (PBS) and resuspended in RPMI 1640 medium with or without eltrombopag at the indicated concentrations. The cell suspension (0.0005 $OD_{600}$/mL) was added to a 96-well polystyrene plate and incubated at 37° C. for 24 or 48 hours. For comparison, *C. neoformans* H99 was cultured similarly in RPMI 1640 medium containing 1 mg/L amphotericin B, 4 mg/L fluconazole, or simply DMSO (control). After incubation, the cells were washed three times with PBS and subjected to XTT reduction assay to quantify formazan formation by FIG. 5B, eltrombopag inhibited the formation of *C. neoformans* biofilms in a dose-dependent manner.

Example 6

Eltrombopag Reduces Capsule Formation of *Cryptococcus*

*Cryptococcus* capsule, the structure attached to the outer surface of the cell wall and mainly composed of polysaccharides, can increase the resistance of *Cryptococcus* to host immune response (such as phagocytosis by macrophages) and harsh conditions (such as extreme acidity or alkalinity, high $CO_2$ levels, or iron deprivation). To test whether eltrombopag affects capsule formation in *Cryptococcus*, *C. neoformans* H99 and *C. deuterogattii* R265 cells were cultured overnight in YPD media at 30° C. The cells were then washed twice with PBS, resuspended in minimal medium containing 0 or 0.06 mg/L eltrombopag, and incubated at 37° C. for 48 hours. Thereafter, the cells were placed on glass slides and counterstained with India ink at room temperature. The stained cells were examined by microscopy and photographed. ImageJ software was used to determine the capsule size of 50 cells randomly selected from each group of cells under different treatments. The capsule size was defined as the distance between the cell wall and outer border of the capsule. The experiments were performed in triplicate, and the results were presented as mean±standard deviation. Statistical significance for the data sets was determined using a two-tailed t test.

Figure 6A:
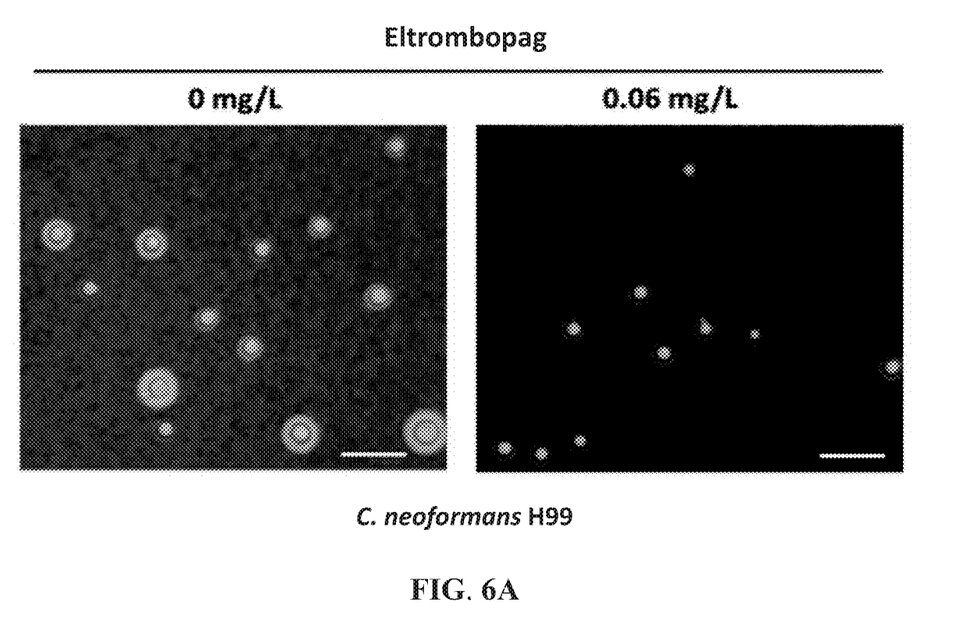
FIG. 6A shows the micrographs of *C. neoformans* H99 after incubation with or without eltrombopag for 48 hours; the scale bars represent 10 μm.
Figure 6B:
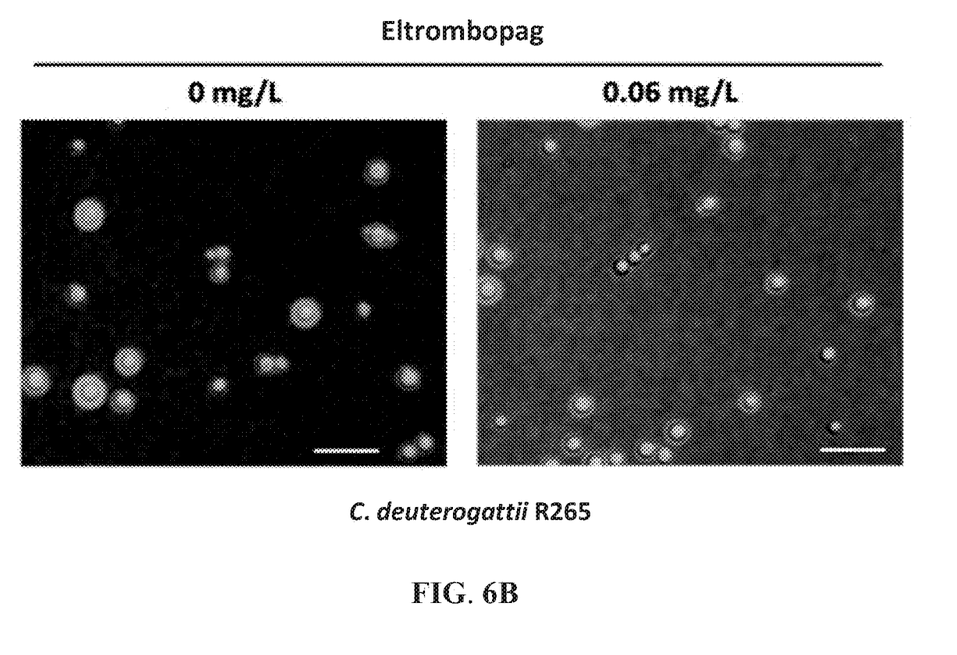
FIG. 6B shows the micrographs of *C. deuterogattii* R265 after incubation with or without eltrombopag for 48 hours; the scale bars represent 10 μm.
Figure 6C:
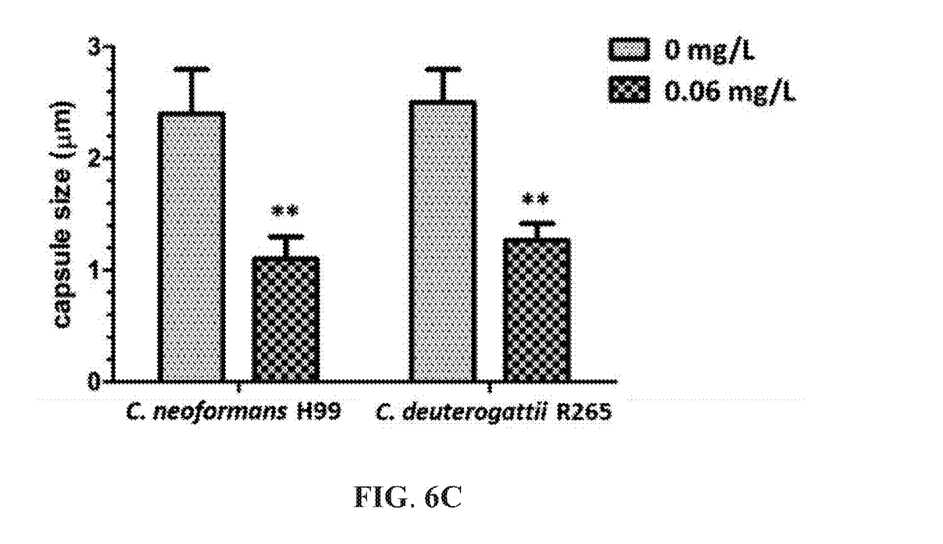
FIG. 6C shows the capsule size in *C. neoformans* H99 or *C. deuterogattii* R265.

FIG. 6A and FIG. 6B are the micrographs of *C. neoformans* H99 and *C. deuterogattii* R265, respectively, after incubation with or without eltrombopag for 48 hours. FIG. 6C shows the capsule size in *C. neoformans* H99 or *C. deuterogattii* R265; ** indicates P<0.01 compared with no eltrombopag treatment. According to FIG. 1, eltrombopag at 0.06 mg/L did not affect the growth kinetics of *Cryptococcus*, indicating that eltrombopag was subinhibitory at approximately below 0.06 mg/L. However, as shown in FIGS. 6A-6C, the capsule size significantly reduced in both *C. neoformans* H99 and *C. deuterogattii* 8265 after 0.06 mg/L eltrombopag treatment versus no eltrombopag treatment. The results suggest that eltrombopag interferes with capsule formation in *Cryptococcus* via a mechanism different from that for inhibiting cryptococcal growth.

Example 7

Eltrombopag Inhibits Melanin Production in *C. neoformans*

Melanin protects *Cryptococcus* from toxic free radicals produced by the host defense system, and thus melanin production is important for the pathogenicity of *Cryptococcus*. To study whether eltrombopag has an effect on melanin production in *Cryptococcus*, $5 \times 10^4$ *C. neoformans* H99 cells were cultured in minimal medium (abbreviated as MM) with or without 1 mM L-DOPA in the presence or absence of eltrombopag. The flasks containing the cultures were wrapped in foil to prevent L-DOPA auto-polymerization. The cultures were incubated at 30° C. with shaking at 150 rpm for ten days in liquid MM and then incubated on solid MM plates in the dark for four days.

Figure 7A:
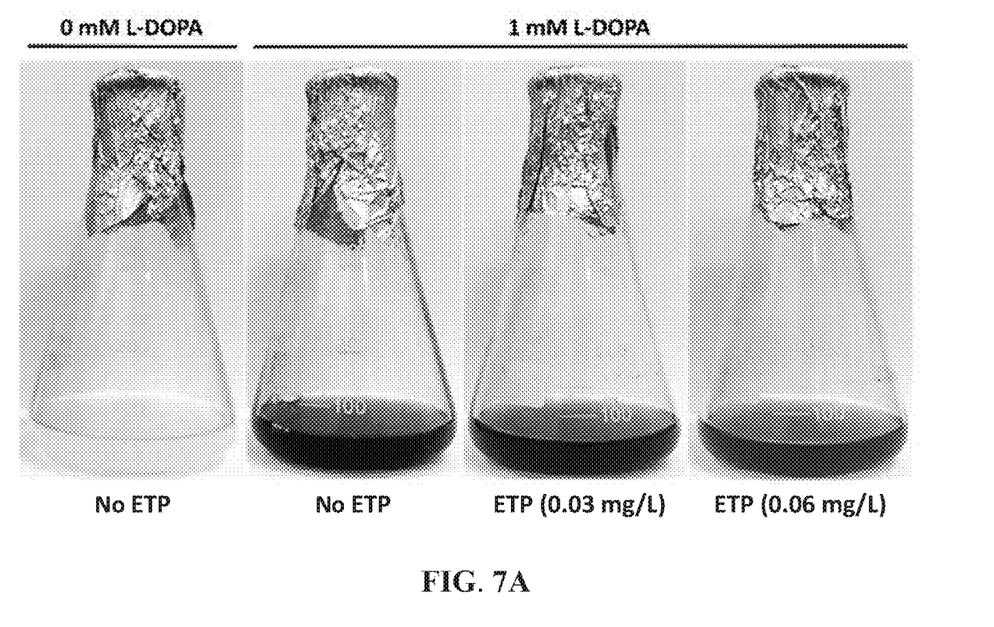
FIG. 7A shows the images of *C. neoformans* H99 after incubation in liquid medium with or without eltrombopag (ETP) for ten days.
Figure 7B:
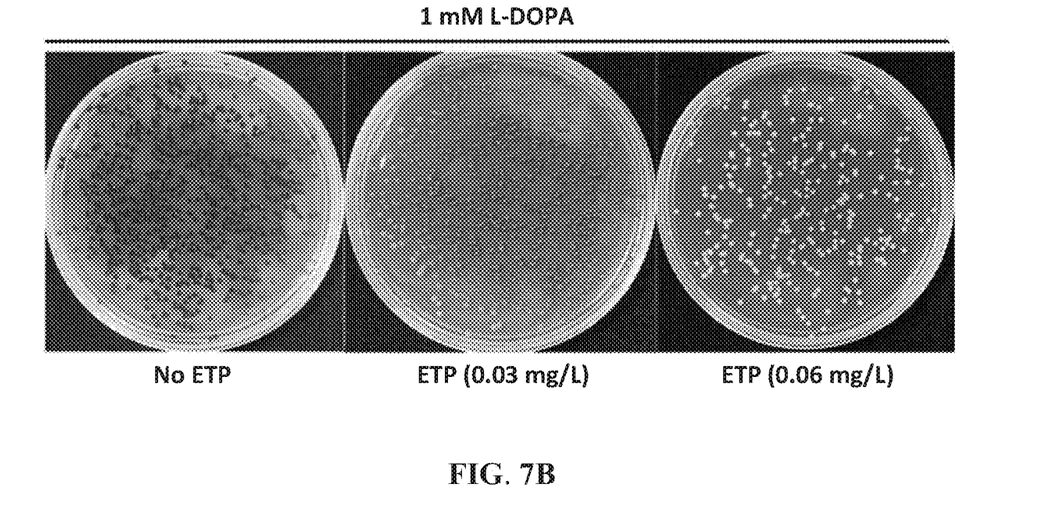
FIG. 7B shows the images of the *C. neoformans* H99 obtained from the cultures shown in FIG. 7A and further incubated on solid plates with or without eltrombopag (ETP) for four days.

FIG. 7A shows the images of *C. neoformans* H99 after incubation in liquid medium with or without eltrombopag (ETP) for ten days; FIG. 7B shows the images of the *C. neoformans* obtained from the cultures shown in FIG. 7A and further incubated on solid plates with or without eltrombopag for four days. According to FIGS. 7A-7B, the culture and the colonies of *C. neoformans* looked dark brown in the absence of eltrombopag; comparatively, in the presence of eltrombopag at 0.03 mg/L (¼ MIC) or 0.06 mg/L (½ MIC), melanin production in *C. neoformans* reduced and thus the culture and the colonies looked light brown. The reduction was more profound when a higher concentration of eltrombopag was applied, indicating that the inhibitory effect of eltrombopag on melanin production is dose-dependent.

In conclusion, the experimental data described above show that eltrombopag is a relatively broad-spectrum antifungal agent capable of inhibiting the growth of various *Cryptococcus* species and other fungi such as *Candida glabrata* and *Trichophyton rubrum*. Particularly, eltrombopag is able to inhibit the growth of azole-resistant clinical *Cryptococcus* strains (for example, the *C. neoformans* T1 and *C. neoformans* 89-610) at an MIC of about 0.125 mg/L, which is lower than the MICs of the existing antifungal drugs fluconazole and amphotericin B. This observation suggests that eltrombopag uses a mode of action distinct from that of azoles to combat *Cryptococcus*. In addition, the combination of eltrombopag and a macrolide calcineurin inhibitor demonstrates synergism in inhibiting the growth of *Cryptococcus*, whereby decreasing the required amounts of the two drugs to inhibit fungi. Eltrombopag can also inhibit the formation of various virulence factors in *Cryptococcus*. Therefore, the invention provides a new method for treatment of fungal infections, particularly cryptococcal infections. The method includes the step of administering an effective amount of eltrombopag or an effective amount of the combination of eltrombopag and a macrolide calcineurin inhibitor to a subject afflicted with fungal or cryptococcal infections.

The present invention has been described with reference to the above preferred embodiments. However, it will be apparent to those skilled in the art that modifications and changes in form and detail may be made without departing from the scope of the present invention defined by the appended claims.

What is claimed is:

1. A method of inhibiting growth of a fungus, comprising contacting the fungus with an effective amount of eltrombopag, wherein the fungus is selected from the group consisting of *Cryptococcus, Candida glabrata*, and *Trichophyton rubrum*.

2. The method of claim 1, wherein the *Cryptococcus* is *Cryptococcus neoformans, Cryptococcus gattii*, or *Cryptococcus deuterogattii*.

3. A combination agent for inhibiting growth of *Cryptococcus*, comprising eltrombopag and a macrolide calcineurin inhibitor.

4. The combination agent of claim 3, wherein the macrolide calcineurin inhibitor is tacrolimus or an analog thereof.

5. A method of inhibiting growth of *Cryptococcus*, comprising contacting the *Cryptococcus* with the combination agent of claim 3.

6. The method of claim 5, wherein the *Cryptococcus* is *Cryptococcus neoformans, Cryptococcus gattii*, or *Cryptococcus deuterogattii*.

7. The method of claim 5, wherein the macrolide calcineurin inhibitor is tacrolimus or an analog thereof.

8. A method of inhibiting virulence factor formation in *Cryptococcus*, comprising contacting the *Cryptococcus* with an effective amount of eltrombopag.

9. The method of claim 8, wherein the *Cryptococcus* is *Cryptococcus neoformans, Cryptococcus gattii*, or *Cryptococcus deuterogattii*.

10. The method of claim 8, wherein the virulence factor formation is biofilm formation.

11. The method of claim 8, wherein the virulence factor formation is capsule formation.

12. The method of claim 8, wherein the virulence factor formation is melanin production.

* * * * *